United States Patent [19]

Hayakawa et al.

[11] Patent Number: 5,053,407

[45] Date of Patent: Oct. 1, 1991

[54] OPTICALLY ACTIVE PYRIDOBENZOXAZINE DERIVATIVES AND ANTI-MICROBIAL USE

[75] Inventors: Isao Hayakawa; Shohgo Atarashi; Masazumi Imamura; Shuichi Yokohama; Nobuyuki Higashihashi; Katsuichi Sakano; Masayuki Ohshima, all of Tokyo, Japan

[73] Assignee: Daiichi Pharmaceutical Co., Ltd., Tokyo, Japan

[21] Appl. No.: 876,623

[22] Filed: Jun. 20, 1986

[30] Foreign Application Priority Data

Jun. 20, 1985 [JP] Japan .................................. 60-134712
Oct. 11, 1985 [JP] Japan .................................. 60-226499
Jan. 28, 1986 [JP] Japan .................................... 61-16496

[51] Int. Cl.$^5$ .................... A61K 31/535; C07D 498/16
[52] U.S. Cl. .................................. 514/230.2; 544/101
[58] Field of Search ...................... 544/101; 514/230.2

[56] References Cited

U.S. PATENT DOCUMENTS 4,382,892  5/1983  Hayakawa et al. ................. 544/101

FOREIGN PATENT DOCUMENTS 0047005  3/1982  European Pat. Off. .
52290  3/1983  Japan .
62-145088  6/1987  Japan .

OTHER PUBLICATIONS

Albrecht et al., Progress in Drug Research, vol. 21 (1971).
Rohlfing et al., J. Antibacterial Chemotherapy (1985).
Gerster et al., Proceedings of the North American Medicinal Chemistry Symposium, (1982).
Hayakawa et al., Chemical & Pharmaceutical Bulletin, vol. 32, No. 13, 1984, pp. 4907–4913, Tokyo, JP.
J. F. Gerster et al., J. Med. Chem., 1987, 30, 839.
Hayakawa et al., "Synthesis and Antibacterial Activities of Optically Active Ofloxacin", vol. 29, No. 1, Jan. 1986, pp. 163–164.

*Primary Examiner*—Richard L. Raymond
*Attorney, Agent, or Firm*—Sughrue, Mion, Zinn, Macpeak & Seas

[57] ABSTRACT

An optically action pyridobenzoxazine derivative, a process for preparing the same and a novel intermediate useful for preparing the optically active pyridobenzoxazine derivative are disclosed. The optically active pyridobenzoxazine derivative possesses increased antimicrobial activity and reduced toxicity. The intermediate is useful for preparing such optically active pyridobenzoxazine derivatives such as Ofloxacin and anolog compounds.

6 Claims, No Drawings

OPTICALLY ACTIVE PYRIDOBENZOXAZINE DERIVATIVES AND ANTI-MICROBIAL USE

FIELD OF THE INVENTION

This invention relates to optically active pyridobenzoxazine derivatives and a process for preparing the same and to novel intermediates useful for preparing such derivatives. More particularly, it relates to optically active compounds of Ofloxacin and its analogs, a process for preparing the same and intermediates useful for preparing the same.

BACKGROUND OF THE INVENTION

Ofloxacin (($\pm$)-9-fluoro-3-methyl-10-(4-methyl-1-piperazinyl)-7-oxo-2,3-dihydro-7H-pyrido[1,2,3-de][1,4]benzoxazine-6-carboxylic acid) is known to be an excellent synthetic antimicrobial agent as disclosed in Japanese Patent Application (OPI) No. 46986/82 (the term "OPI" used herein means "unexamined published patent application").

Ofloxacin has an asymmetric carbon atom at the 3-position thereof and is obtained as a racemate (specific rotation $[\alpha]_D = 0°$) by known processes. The present inventors obtained optically active compounds of the racemic Ofloxacin and found that the S($-$)-compound possesses an antimicrobial activity of about 2 times higher than that of the ($\pm$)-compound and an acute toxicity (LD$_{50}$) weaker than that of the ($\pm$)-compound as determined in mice by intravenous administration. On the other hand, the present inventors found that the R($+$)-compound exhibits an antimicrobial activity of only about 1/10 to 1/100 times that of the ($\pm$)-compound, whereas it possesses an acute toxicity substantially equal to that of the ($\pm$)-compound. That is, the S($-$)-form of Ofloxacin has been found to have very desirable properties, i.e., increased antimicrobial activity and reduced toxicity, and is expected to be a very useful pharmaceutical agents as compared with the ($\pm$)-compound. Further, both the R($+$)- and S($-$)-compounds of Ofloxacin in the free form have markedly high water-solubility as compared with ($\pm$)-compound and as compared with free compounds of this type, and can be used as injectable preparations. These advantages will be apparent from the experimental data shown hereinafter.

SUMMARY OF THE INVENTION

As a result of investigations with the purpose of preparing, especially S($-$)-form having higher activity, among the two isomers of Ofloxacin, it has now been found that compounds having the following formula (X) are useful as intermediates for synthesizing an isomer of Ofloxacin as well as other isomers of pyridobenzoxazine derivatives having excellent antimicrobial activity:

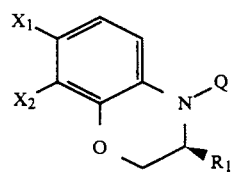

wherein $X_1$ and $X_2$, which may be the same or different, each represents a halogen atom, such as a fluorine atom, a chlorine atom, and preferably both $X_1$ and $X_2$ are fluorine atoms; $R_1$ represents an alkyl groups having from 1 to 4 carbon atoms, such as a methyl group, an ethyl group, a propyl group, etc., and preferably a methyl group; Q represents a hydrogen atom or a group

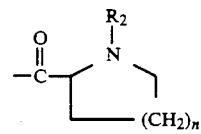

wherein $R_2$ represents a substituted sulfonyl group, an alkoxycarbonyl group or an aralkyloxycarbonyl group, such as a p-toluenesulfonyl group, a benzenesulfonyl group, a methanesulfonyl group, a t-butoxycarbonyl group, a benzyloxycarbonyl group, a p-methoxybenzyloxycarbonyl group, etc., preferably a substituted sulfonyl group, and more preferably a p-toluenesulfonyl group; and n represents an integer of from 1 to 3, and preferably 1 or 2.

An object of this invention is to provide optically active Ofloxacin and its analogs.

Another object of this invention is to provide a novel intermediate represented by the above-described formula (X) which is useful for synthesizing optically active Ofloxacin and other pyridobenzoxazine derivatives.

A still another object of this invention is to provide a novel process for preparing optically active Ofloxacin and its analogs by the use of the above-described intermediate.

DETAILED DESCRIPTION OF THE INVENTION

The optically active Ofloxacin and its analogs according to the present invention can be represented by the formula (VI):

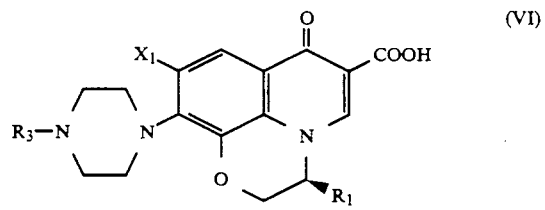

wherein $X_1$ and $R_1$ are as defined above, and $R_3$ represents an alkyl group having 1 to 3 carbon atoms.

In the above-described formula (VI), $X_1$ preferably represents a fluorine atom, and $R_1$ preferably represents a methyl group, and $R_3$ preferably represents a methyl group or an ethyl group.

The optically active Ofloxacin and its analogs of the invention can be prepared by any of Processes A, B and C shown below:

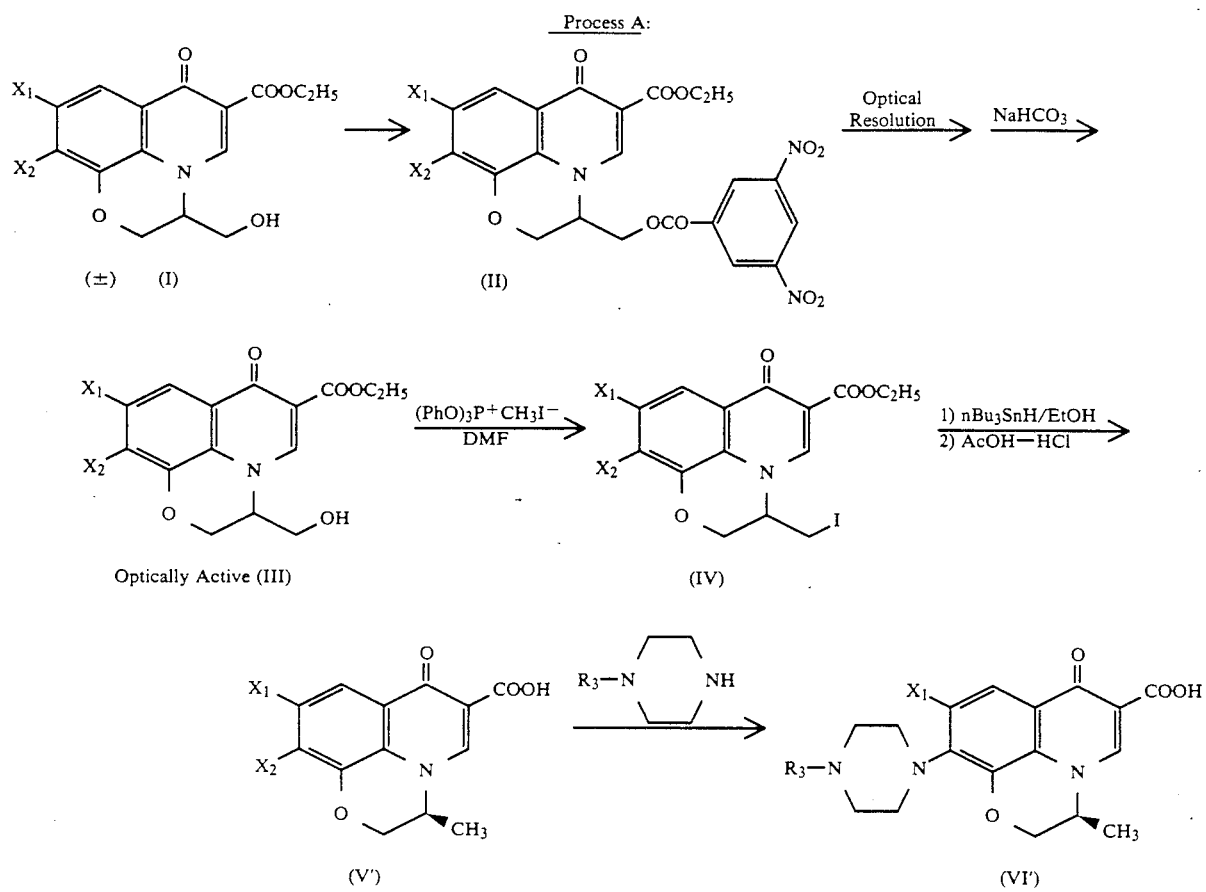

Process A:

wherein $X_1$, $X_2$ and $R_3$ are as defined above.

More specifically, the (±)-3-hydroxymethyl compound (I) is treated with 3,5-dinitrobenzoyl chloride, etc. to obtain its derivative, such as the (±)-3,5-dinitrobenzoate compound (II), which is then optically resolved into two optically active compounds by an appropriate method, such as high performance liquid chromatography (HPLC). The subsequent procedures can be applied to either of the S(−)-compound and the R(+)-compound to lead to the respective final product, but in view of the purpose of the present invention, the final product (VI') is shown as S(−)-form.

The resulting optically active compound is treated with sodium hydrogencarbonate, etc. to selectively hydrolyzing the benzoate moiety to form the hydroxymethyl compound (III). The hydroxymethyl compound is converted into the 3-iodomethyl compound (IV) by using a iodinating reagent, which is then reduced with n-tributyltin hydride, etc. to prepare the 3-methyl compound. This compound, without being isolated and purified, can be hydrolyzed as such under an acidic condition to obtain the 3-methyl-6-carboxylic acid (V'). The carboxylic acid is then reacted with an N-alkylpiperazine by, for example, heating while stirring to obtain the 10-(4-alkylpiperazinyl) compound (VI') as a final product.

The compounds of the formula (VI) wherein $R_1$ represents an alkyl group other than the methyl group can also be prepared in the same manner from an appropriate (±)-3-hydroxyalkyl compound of the formula (I).

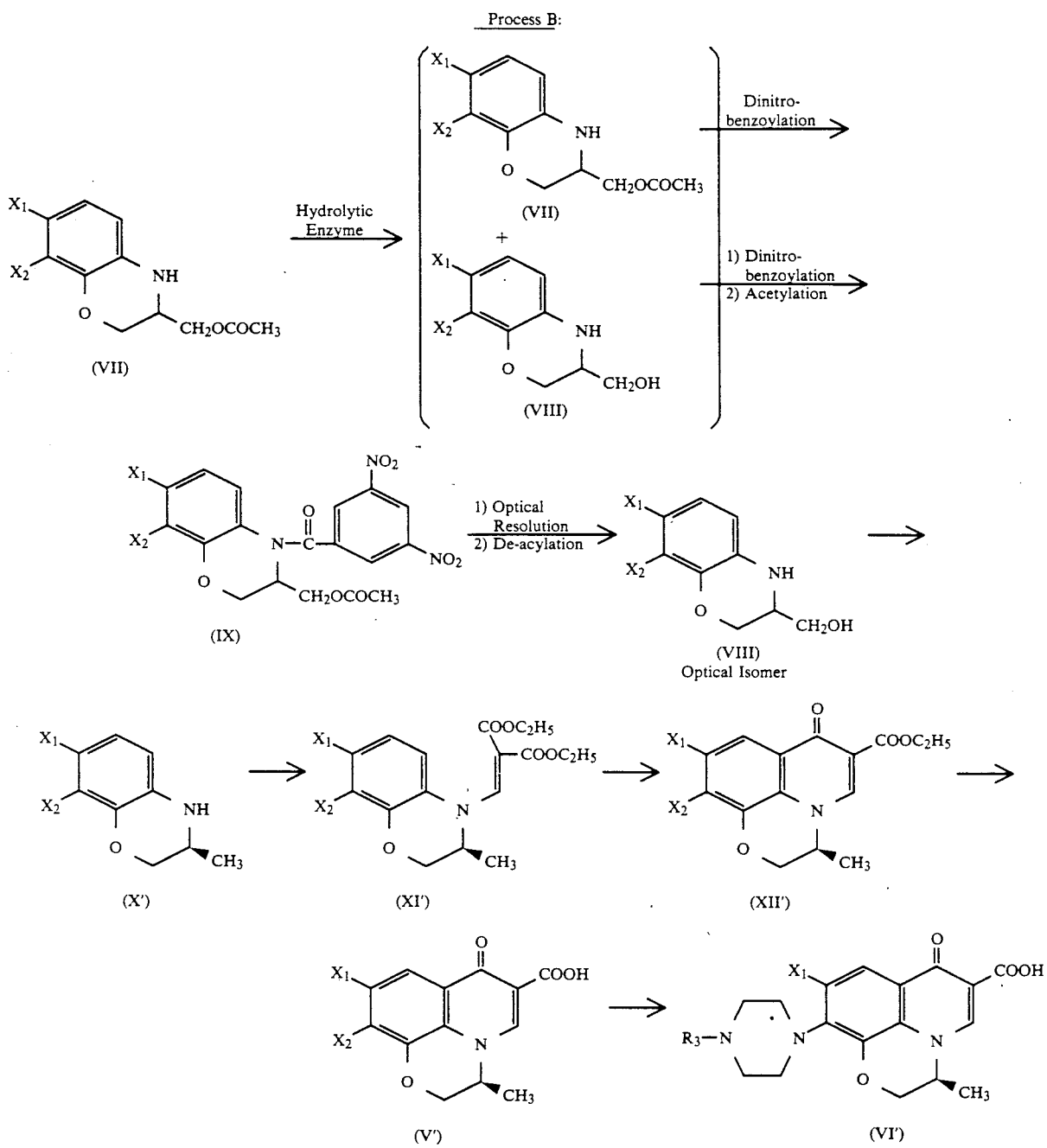

wherein $X_1$, $X_2$ and $R_3$ are as defined above.

As described previously, 7,8-difluoro-2,3-dihydro-3-methyl-4H-[1,4]benzoxazine having the formula (X) wherein $X_1$ and $X_2$ represent fluorine atoms, Q represents a hydrogen atom and $R_1$ represents a methyl group is an important intermediate for synthesizing Ofloxacin. The inventors have conducted various investigations on an advantageous process for preparing an optical isomer of this compound expecting that such would be a useful starting material for synthesizing the S(−)-isomer of Ofloxacin.

As a result, it has been found that when a racemic 7,8-dihalogeno-2,3-dihydro-3-acetoxymethyl-4H-[1,4]benzoxazine (VII), as a substrate, is hydrolyzed with an appropriate enzyme, such as a certain kind of lipase, to form a 7,8-dihalogeno-2,3-dihydro-3-hydroxymethyl-4H-[1,4]benzoxazine (VIII), there is a difference in the rate of hydrolysis between the (+)-isomer and the (−)-isomer.

For example, the compound (VII) was reacted with lipoprotein lipase (LPL Amano 3 derived from *Pseudomonas aeruginosa*, produced by Amano Seiyaku K.K.) or lipase (derived from *Porcine pancreas*, produced by Shigma Chemical Company (U.S.A.); derived from *Candida cylindracea*, produced by Shigma Chemical Company; or derived from *Rhizopus delemar*, produced by Seikagaku Kogyo Co., Ltd.), and the reaction change with time was determined through HPLC (column: TSK gel ODS-120A, 4.6×250 mm; solvent: acetonitrile/water=1/1 by volume; velocity: 1 ml/min). When the rate of hydrolysis reached about 55%, the compound (VII) was recovered and led to a 3,5-dinitrobenzoyl derivative (IX). The resulting reaction product was quantitatively determined by HPLC (column: Sumipacks OA-4200, 4.0×250 mm; solvent: n-hexane/1,2-dichloroethane/ethanol=92/6.4/1.6 by volume; velocity: 1.6 ml/min) to obtain a ratio of the (+)-isomer/(−)-isomer of the compound (VII). The results obtained were shown in Table 1 below.

TABLE 1

| Enzyme (Origin) | Rate of Hydrolysis (%) | (+)/(−) |
|---|---|---|
| LPL Amano 3 (P. aeruginosa) | 54.7 | 23.0/77.0 |
| Lipase (R. delemar) | 53.6 | 42.6/57.4 |
| Lipase (C. cylindracea) | 54.5 | 61.9/38.1 |
| Lipase (P. pancreas) | 55.2 | 56.8/43.2 |

These results lead to a conclusion that the optically active compounds (VII) and (VIII) can be obtained by utilizing the so-called asymmetric hydrolysis with these enzymes.

Process B according to the present invention comprises reacting a racemic 7,8-dihalogeno-2,3-dihydro-3-acetoxymethyl-4H-[1,4]benzoxazine (VII) with an asymmetric hydrolytic enzyme to recover a mixture comprising the starting compound (VII) rich in either one of optical isomers and a 3-hydroxymethyl compound (VIII), separating the mixture into each compound, dinitrobenzoylating either one or both of these compounds and further acetylating the benzoylated 3-hydroxymethyl compound (VIII) to obtain the compound (IX), separating the compound into a racemate and an optical isomer by crystallization, subjecting the resulting optical isomer to deacylation and dehydroxylation by means of known chemical processes to obtain an optically active 7,8-dihalogeno-2,3-dihydro-3-methyl-4H-[1,4]benzoxazine (X') and then obtaining therefrom optically active Ofloxacin or its analog (VI') by known processes.

Process B of the invention will further be illustrated in some detail referring to specific examples.

The racemic compound (VII) is dissolved in a 0.1M phosphoric acid buffer (pH 7.0), and lipoprotein lipase (LPL Amano 3) is added to the solution to cause enzymatic reaction at 37° C. By this reaction, the (+)-compound is preferentially hydrolyzed to thereby form a mixture of the compound (VII) rich in the (−)-isomer and the compound (VIII) rich in the (+)-isomer. The reaction mixture is recovered in an appropriate stage by extraction with an organic solvent, such as ethyl acetate.

The above enzymatic reaction may also be carried out in an appropriate organic solvent, such as a mixed solvent of benzene and n-hexane, by using a hydrophilic resin, e.g., DEAE-Toyopearl 650M or Toropearl HW-40, etc., or Celite as a dispersing agent or by using a resin, such as Amberlite XAD-7, Butyl-Toyopearl 650M, etc., as an adsorptive fixing agent. In addition, use of inclusive fixing agents, such as photo-crosslinked resins, urethane prepolymers, etc., is also considered to make it possible to effect the enzymatic reaction in an organic solvent.

The reaction in an organic solvent with an aid of appropriate dispersing agents or fixing agents as described above is advantageous in that the substrate can be reacted at higher concentrations than in an aqueous solution and that post-treatments after the reaction can be simplified. Actually, in the case of performing the reaction in an organic solvent, the reaction mixture can be recovered in high yields simply by filtering the dispersing agent or fixing agent in an appropriate stage and concentrating the filtrate. Moreover, the fixing agents can be repeatedly reused to advantage.

The compounds (VII) and (VIII) in the reaction mixture can be separated and purified by a usual method of separation, such as silica gel column chromatography. The thus separated compound (VII) is treated, for example, with 3,5-dinitrobenzoyl chloride in tetrahydrofuran in the presence of pyridine to form the 3,5-dinitrobenzoyl derivative (IX), which is then recrystallized from an appropriate solvent, e.g., a mixed solvent of ethyl acetate and n-hexane, whereby the racemate is preferentially crystallized. The racemic crystals are separated by filtration, and the (−)-7,8-dihalogeno-2,3-dihydro-3-acetoxymethyl-4H-[1,4]benzoxazine 3,5-dinitrobenzoyl derivative (IX) having a high optical purity is obtained from the filtrate.

The compound (IX) is then subjected to de-acylation treatment by, for example, hydrolysis under an alkaline condition to form the (−)-isomer of the compound (VIII). This compound is dissolved in pyridine and treated with thionyl chloride, and the product is further subjected to dehydroxylation in a usual manner, such as reduction with sodium borohydride in dimethyl sulfoxide, to thereby obtain the (−)-7,8-dihalogeno-2,3-dihydro-3-methyl-4H-[1,4]benzoxazine (X') having an optical purity of 99% or higher.

When the racemic compound (VII) is treated with lipase (derived from Candida cylindracea or Porcine Pancreas), the (−)-compound is preferentially hydrolyzed to obtain the compound (VIII) rich in the (−)-isomer. The resulting compound is led to a compound in the form of the compound (IX), which is then treated in accordance with the procedures as described above, such as separation by crystallization, to form the (−)-isomer of the compound (VIII). The (−)-isomer of the compound (X') can then be prepared from this product in the same manner as described above with a high purity.

Other asymmetric hydrolyses which can achieve the object of the present invention in addition to the above-recited enzymes can be found based on the above-mentioned elucidation. Further, when it is intended to obtain (+)-compounds, the same procedures as described above can be followed based on the above elucidation.

The (−)-compound of Ofloxacin and analogs thereof can be prepared from the novel intermediates of the present invention having the formula (X') in accordance with Process C as illustrated below.

Process C:

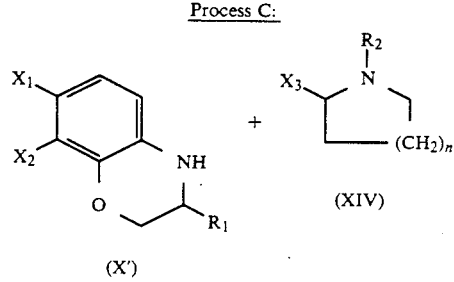

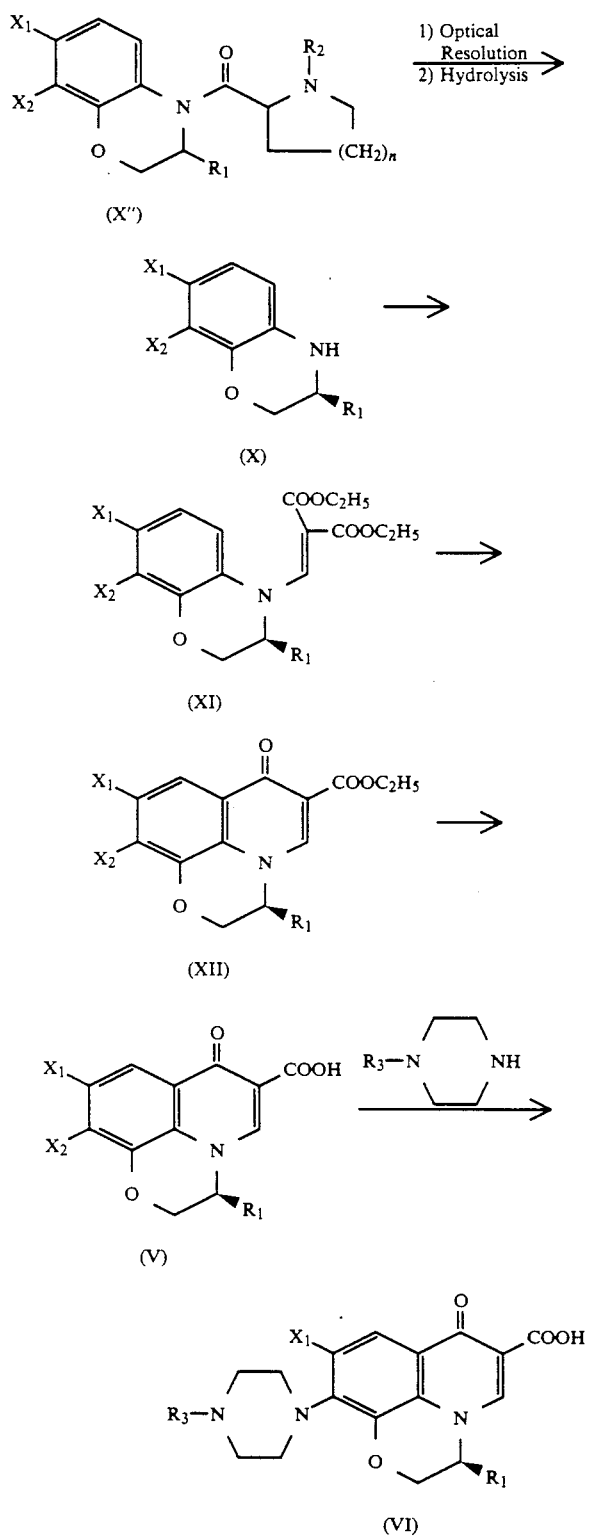

wherein n, $X_1$, $X_2$, $R_1$, $R_2$ and $R_3$ are as defined above, and $X_3$ is a carboxyl group or a reactive derivative thereof, for example, an active ester, a halide or an acid anhydride of the carboxylic acid.

In Process C, the 7,8-dihalogeno-1,4-benzoxazine derivative (X') is condensed with a cyclic amino acid or a reactive derivative thereof (XIV) through amide linkage formation to produce the compound (X''). The condensation reaction can be effected by either one of the active ester method, the acid anhydride method or the DCC method, but, generally, the compound (X') and an acid chloride (XIV) wherein $X_3$ is —COCl are reacted in an organic solvent such as halogenated hydrocarbons, e.g., dichloromethane, in the presence of an acid acceptor such as pyridine, triethylamine or potassium carbonate, at room temperature while stirring. The reaction product can be isolated and purified in a conventional manner, such as crystallization, column chromatography, etc.

In this condensation reaction, when either one of the two isomers of the cyclic amino acid or its reactive derivative (XIV), i.e., an S-compound or an R-compound, is used, separation of the diasteromeric mixture of the compound (X'') can be carried out easily. More specifically, derivatives (XIV), such as S- or R-proline, S- or R-pipecolic acid (piperidine-2-carboxylic acid), etc., are suitably used. The most preferred compounds (XIV) include (S)-N-benzenesulfonylproline and (S)-N-p-toluenesulfonylproline.

The diastereomeric mixture of the compound (X'') can be separated by fractional crystallization, chromatography using silica gel, etc. as a carrier, or a combination thereof.

The thus separated diastereomer is hydrolyzed, usually under a basic condition, to form a 7,8-dihalogeno-3-(S or R)-lower alkyl-[1,4]benzoxazine (X). This compound can be led to a 9,10-dihalogeno-3-(S or R)-lower alkyl-7-oxo-2,3-dihydro-7H-pyrido[1,2,3-de][1,4]benzoxazine-6-carboxylic acid (V) through known reactions, which can then be converted to a 10-(4-alkyl-piperazinyl) compound (VI).

Of the above-described Processes A, B and C, the particularly preferred is Process C.

Antimicrobial Activity

The antimicrobial activities of the optical isomers [(—) and (+)] of Ofloxacin and an analog compound to various microorganisms were compared with that of Ofloxacin (racemate), and the results are shown in Table 2 below. The test method was in accordance with the standard method specified by The Japan Society of Chemotherapy.

TABLE 2

| | Minimum Inhibitory Concentration (MIC; μg/ml) | | | |
|---|---|---|---|---|
| Microorganism | S(—)-Ofloxacin* | Racemic Ofloxacin | R(+)-Ofloxacin | Compound of Example 17 |
| E. coli, NIHJ | <0.1 | <0.10 | 0.39 | <0.1 |
| K. pneumoniae, Type 2 | <0.1 | 0.10 | 1.56 | <0.1 |
| Ser. marcescens, 10100 | <0.1 | 0.10 | 1.56 | <0.1 |

TABLE 2-continued

| Microorganism | Minimum Inhibitory Concentration (MIC; μg/ml) | | | |
|---|---|---|---|---|
| | S(−)-Ofloxacin* | Racemic Ofloxacin | R(+)-Ofloxacin | Compound of Example 17 |
| Ps. aeruginosa, 32104 | 0.39 | 0.78 | 12.5 | 0.39 |
| Ps. aeruginosa, 32121 | 0.10 | 0.20 | 6.25 | 0.10 |
| Ps. maltophilia, IID1275 | 0.39 | 0.78 | 12.5 | 0.10 |
| S. aureus, Smith | 0.10 | 0.20 | 6.25 | <0.1 |
| S. aureus, 209P | 0.20 | 0.39 | 25 | 0.10 |
| Str. pyogenes, G-36 | 0.78 | 1.56 | <100 | 1.56 |

Acute Toxicity

The acute intravenous toxicity of (±), R(+) and S(−)-forms of Ofloxacin in male mice is shown in Table 3 below.

TABLE 3

| Compounds | Dose (mg/kg) | Numbers of mice | Day after treatment | | | Mortality |
|---|---|---|---|---|---|---|
| | | | 1 | 2 | 3 | |
| (±) | 100 | 5 | 0 | 0 | 0 | 0/5 |
| | 200 | 5 | 2 | 0 | 0 | 2/5 |
| | 400 | 5 | 5 | 0 | 0 | 5/5 |
| R(+) | 100 | 5 | 0 | 0 | 0 | 0/5 |
| | 200 | 5 | 3 | 0 | 0 | 3/5 |
| | 400 | 5 | 5 | 0 | 0 | 5/5 |
| S(−) | 100 | 5 | 0 | 0 | 0 | 0/5 |
| | 200 | 5 | 0 | 0 | 0 | 0/5 |
| | 400 | 5 | 5 | 0 | 0 | 5/5 |

LD$_{50}$ (i.v. in mice)
(±)-form 203 mg/kg
S(−)-form 244 mg/kg

Solubility

The solubility of (±), R(+) and S(−)-forms of Ofloxacin in water at a temperature in the range of from 23° to 26° C. is shown in Table 4 below.

TABLE 4

| Compounds | Water-Solubility (μg/ml) |
|---|---|
| (±) | 2,400 |
| R(+) | 25,800 |
| S(−) | 22,500 |

The conversion of the intermediates of the formula (X) into the desired Ofloxacin or an analog thereof can be carried out by a well known process as disclosed, for example, in U.S. Pat. No. 4,382,892, EPC Patent 47005, Japanese Patent Application (OPI) Nos. 29789/83 and 43977/82.

This invention will now be illustrated in greater detail with reference to the following examples, but it should be understood that they are not intended to limit the present invention. Examples 1 to 7 describe preparation of Ofloxacin according to Process A; Examples 8 to 11 describe preparation of Ofloxacin according to Process B; and Examples 12 to 17 describe preparation of Ofloxacin and analog compounds according to Process C.

EXAMPLE 1

Preparation of Benzoyloxy Compound

One gram of (±)-9,10-difluoro-3-hydroxymethyl-7-oxo-2,3-dihydro-7H-pyrido[1,2,3-de][1,4]benzoxazine-6-carboxylic acid ethyl ester (I) and 500 mg of pyridine were suspended in 100 ml of anhydrous tetrahydrofuran (THF), and 1.6 g of 3,5-dinitrobenzoyl chloride was added thereto, followed by refluxing at 90° C. The suspension was once dissolved, and a colorless precipitate was then formed. The reaction was continued for 1.5 hours. After cooling, the precipitate was collected by filtration, washed with methanol and diethyl ether and dried to obtain 1.2 g of (±)-9,10-difluoro-3-(3,5-dinitrobenzoyloxy)methyl-7-oxo-2,3-dihydro-7H-pyrido[1,2,3-de][1,4]benzoxazine-6-carboxylic acid ethyl ester (II) as a colorless powder having a melting point of 240°-242° C.

NMR (CDCl$_3$/5% DMSO-d$_6$) δ(ppm); 1,30 (3H, t, J=7.0Hz, —CH$_2$CH$_3$), 4.26 (2H, q, J=7.0Hz, —CH$_2$CH$_3$), 4.4–4.5 (5H, m), 7.76 (1H, dd, J=11.0Hz, 7.0Hz, C$_8$—$\underline{H}$), 8.8 (1H, s, C$_5$—$\underline{H}$), 9.0 (2H, d, J=3.0Hz, aromatic ring proton) and 9.2 (1H, t, J=3.0Hz, aromatic ring proton)

EXAMPLE 2

Optical Resolution

Six milligrams of the benzoyloxy compound as obtained in Example 1 was dissolved in about 0.6 ml of dimethylformamide (DMF) which had been purified by distillation. The solution was filtered through a millipore filter and subjected to HPLC using a column of Sumipacks OA-4200 (2 cm×25 cm) and a solvent of n-hexane/1,2-dichloroethane/ethanol=6/3/1 (by volume) at a velocity of 8 ml/min.

Since the initial fractions (fractions of the (+)-compound) contained a slight amount of the racemic compound (I) due to partial hydrolysis when dissolved in DMF, they were further purified by silica gel chromatography using chloroform to 10% methanol/-chloroform as an eluent. These purification procedures were repeated to thereby obtain 250 mg each of the two optically active compounds [(−)-isomer and (+)-isomer] from 600 mg of the benzoyloxy compound (II).

(+)-Isomer: retention time: 56–76 mins. (column temperature: 22° C.); melting points: 235°-240° C.; $[\alpha]_D^{23}$ = +90.8° (c=0.852, DMF)

(−)-Isomer: retention time: 78–98 mins. (column temperature: 22° C.); melting points: 244°-249° C.; $[\alpha]_D^{23}$ = −92.5° (c=0.889, DMF)

EXAMPLE 3

Preparation of Ethyl (−)-9,10-Difluoro-3-Hydroxymethyl-7-Oxo-2,3-Dihydro-7H-Pyrido[1,2,3-de][1,4]Benzoxazine-6-Carboxylate (III)

In a mixture of 10 ml of ethanol and 4 ml of a saturated aqueous solution of sodium bicarbonate, 120 mg of the optically active benzoyloxy compound [(−)-isomer] was suspended, and the suspension was heated at 50° to 60° C. for 2 hours while stirring. After concentration, water was added to the reaction mixture, and any insoluble material was collected by filtration, washed successively with water, 95% ethanol and diethyl ether to obtain 68 mg of an optically active 3-hydroxymethyl compound [(III), (−)-isomer] as a colorless crystal having a melting point of 235°-240° C.

Elementary Analysis for $C_{15}H_{13}F_2NO_5$: Calcd. (%): C 55.39, H 4.03, N 4.31. Found (%): C 55.44, H 4.01, N 4.49.

$[\alpha]_D^{23} = -125.9°$ (c=0.918, DMF)

In the same manner as described above, a (+)-3-hydroxymethyl compound was synthesized from the (+)-benzoyloxy compound. Melting point: 231°–234° C. $[\alpha]_D^{23} = +125.9°$ (c=0.715, DMF).

EXAMPLE 4

Preparation of Ethyl (−)-9,10-Difluoro-3-Iodomethyl-7-oxo-2,3-Dihydro-7H-Pyrido-[1,2,3-de][1,4]Benzoxazine-6-Carboxylate (IV)

In 12 ml of anhydrous DMF was suspended 63 mg of the (−)-3-hydroxymethyl compound (III), and the suspension was heated at 70° to 80° C. with stirring to form a solution, followed by allowing to cool to room temperature. To the solution was added 340 mg of triphenylphosphite methiodide, followed by stirring for 1.5 hours. The solvent was removed by distillation under reduced pressure, and the residue was dissolved in chloroform. The solution was partitioned with a sodium thiosulfate aqueous solution and then with a saturated sodium chloride aqueous solution. The chloroform layer was dried over anhydrous magnesium sulfate, and the solvent was removed by distillation. To the residue was added diethyl ether, followed by stirring, and the precipitated solid was collected by filtration, washed with diethyl ether and dried under reduced pressure to obtain 78 mg of an iodomethyl compound (IV) as a white powder having a melting point of 214°–217° C.

Elementary Analysis for $C_{15}H_{12}F_2INO_4$: Calcd. (%): C 41.40, H 2.78, N 3.22 Found (%): C 41.16, H 2.58, N 2.99

The (+)-compound was obtained in the same manner as described above.

EXAMPLE 5

Preparation of S(−)-9,10-Difluoro-3-Methyl-7-Oxo-2,3-Dihydro-7H-Pyrido-[1,2,3-de][1,4]-Benzoxazine-6-Carboxylic Acid (V')

In 18 ml of absolute ethanol was suspended 78 mg of the iodomethyl compound (IV), and the suspension was heated at 60° to 70° C. with stirring to form a solution, followed by allowing to cool to room temperature. To the resulting solution was added 0.2 ml of n-tributyltin hydride, and the mixture was stirred at 50° to 60° C. for 1 hour and then at room temperature for 1 hour. The solvent was removed by distillation, and the residue was subjected to column chromatography using 8 g of silica gel as a carrier and chloroform:methanol (40:1 by volume) as an eluent to obtain a crude methyl compound. The crude product was dissolved in 2 ml of glacial acetic acid, and 4 ml of concentrated hydrochloric acid was added thereto. After heating at reflux for 40 minutes, the reaction mixture was concentrated. Water was added to the concentrate, and the thus precipitated crystal was collected by filtration, washed successively with water, ethanol and diethyl ether and dried under reduced pressure to obtain 22 mg of crystals of a S(−)-compound (V') having a melting point of 300° C. or higher.

Elementary Analysis for $C_{13}H_9F_2NO_4$: Calcd. (%): C 55.52, H 3.23, N 4.98 Found (%): C 55.79, H 3.20, N 4.91

$[\alpha]_D^{23} = -65.6°$ (c=0.950, DMSO)

EXAMPLE 6

Preparation of S(−)-9-Fluoro-3-Methyl-10-(4-Methyl-1-Piperazinyl)-7-Oxo-2,3-Dihydro-7H-Pyrido[1,2,3-de][1,4]Benzoxazine-6-Carboxylic Acid In 3 ml of anhydrous dimethyl sulfoxide were dissolved 21 mg of the S(−)-9,10-difluoro-3-methyl-6-carboxylic acid (V') and 30 mg of N-methylpiperazine, and the solution was stirred at 130° to 140° C. for 1 hour. The solvent was removed by distillation, and to the residue was added 2 ml of ethanol. The thus precipitated solid was collected by filtration and washed successively with a small amount of ethanol and diethyl ether. The resulting powder weighing 14 mg was passed through a column of 5 g of silica gel and eluted with a lower layer solution of chloroform-methanol-water (7:3:1 by volume) to obtain the titled compound, 10-(4-methyl-1-piperazinyl) compound (VI'). The mother liquor left after the filtration was subjected to thin layer chromatography (silica gel; 20 cm×20 cm, 5 mm (t)) and developed with a lower layer solution of chloroform-methanol-water (15:3:1 by volume). Both the purified products were combined to yield 14 mg of the titled compound as a crystal having a melting point of 220°–228° C. (with decomposition).

Elementary Analysis for $C_{18}H_{20}FN_3O_4$: Calcd. (%): C 59.82, H 5.58, N 11.63 Found (%): C 60.01, H 5.69, N 11.53

$[\alpha]_D^{24} = -68.8°$ (c=0.711, 0.05N NaOH)

MS (m/e): 361 (M+)

NMR (CDCl$_3$) δ(ppm): 1.63 (3H, d, C$_3$—CH$_3$), 2.38 (3H, s, N—CH$_3$), 2.54-2.6 (4H, m, 2×CH$_2$N), 3.4-3.44 (4H, m, 2×$\overline{CH_2}$N), 4.35-4.52 (3H, m, $\overline{CH}$ and CH$_2$), 7.76 (1H, d, aromatic ring C$_8$—$\underline{H}$) and 8.64 (1$\overline{H}$, s, C$_5$—$\underline{H}$)

The (+)-compound was obtained in the same manner as described above. Melting point: 218°–226° C. (with decomposition). $[\alpha]_D^{24} = +68.7°$ (c=0.560, 0.05N NaOH). MS (m/e): 361 (M+).

EXAMPLE 7

Preparation of S(−)-9-Fluoro-3-Methyl-10-(4-Methyl-1-Piperazinyl)-7-Oxo-2,3-Dihydro-7H-Pyrido[1,2,3-de][1,4]Benzoxazine-6-Carboxylic Acid (VI')

In 30 ml of diethyl ether was suspended 281 mg of the (−)-9,10-difluoro-3-methyl-6-carboxylic acid (V') as obtained in Example 5, and a large excess of boron trifluoride ethyl etherate was added thereto while stirring at room temperature, followed by allowing the mixture to react for 45 minutes. The precipitate formed was collected by filtration, washed with diethyl ether and dried under reduced pressure. The resulting chelate compound weighing 310 mg was dissolved in 6 ml of dimethyl sulfoxide, and 0.32 ml of triethylamine and 0.13 ml of N-methylpiperazine were added to the solution. The mixture was stirred at room temperature for 17 hours, followed by concentration to dryness under reduced pressure. The residue was washed with diethyl ether and then dissolved in 20 ml of 95% ethanol containing 0.5 ml of triethylamine, and the solution was heated at reflux for 8 hours. After cooling, the reaction mixture was concentrated to dryness under reduced pressure. The residue was dissolved in 5% diluted hydrochloric acid, and the solution was distributed between chloroform and water. The aqueous layer was adjusted to a pH of 11 with 1N sodium hydroxide and then to a pH of 7.4 with 1N hydrochloric acid. The solution was extracted three times with 50 ml portions of chloroform, and the extract was dried over sodium sulfate. The chloroform was removed by distillation. Recrystallization of the resulting powder from ethanol-diethyl ether gave 120 mg of the titled compound as a transparent fine needle-like crystal having a melting point of 225°–227° C. (with decomposition). $[\alpha]_D^{24} = -76.9°$ (c=0.385, 0.05N NaOH)

Elementary Analysis for $C_{18}H_{20}FN_3O_4 \cdot \frac{1}{2}H_2O$: Calcd. (%): C 58.37, H 5.72, N 11.35 Found (%): C 58.17, H 5.58, N 11.27

REFERENCE EXAMPLE 1

Preparation of (±)-3-Acetoxymethyl-7,8-Difluoro-2,3-Dihydro-4H-[1,4]Benzoxazine

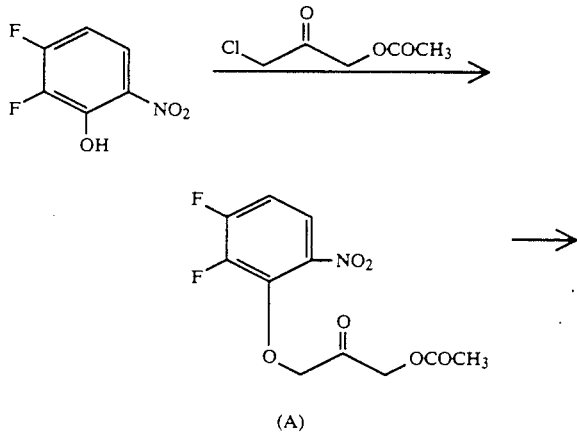

In 1.0 liter of acetone was dissolved 60.0 g of 2,3-difluoro-6-nitrophenol, and 70.0 g of 1-acetoxy-3-chloro-2-propane and then 33.1 g of potassium carbonate were added to the solution while stirring at room temperature. After stirring for an addirional 30 k minutes, 6.6 g of potassium iodide was added thereto, and the mixture was refluxed for 4 hours. After allowing to cool, the reaction mixture was filtered, and the filtrate was concentrated under reduced pressure. The concentrate was dissolved in 4.0 liters of a mixed solvent of ethyl acetate:benzene (1:1 by volume). The resulting solution was washed with water, dried over anhydrous sodium sulfate and concentrated under reduced pressure. The concentrate was subjected to column chromatography using 1.2 Kg of silica gel and benzene/ethyl acetate (10/1) as an eluent to obtain 32.8 g of Compound (A) as an oily product. Compound (A) was dissolved in 300 ml of methanol, and 115 ml of Raney nickel was added thereto to effect catalytic reduction under atmospheric pressure. The reaction mixture was filtered, and the filtrate was concentrated under reduced pressure. The concentrate was purified by column chromatography by using 400 g of silica gel and benzene/ethyl acetate (10/1 by volume) as an eluent, and the product was recrystallized from benzene-n-hexane to obtain 17.9 g of (±)-3-acetoxymethyl-7,8-difluoro-2,3-dihydro-4H-[1,4]benzoxazine (VII) as a colorless crystal having a melting point of 73°–74° C.

Elementary Analysis for $C_{11}H_{11}F_2NO_3$: Calcd. (%): C 54.32, H 4.56, N 5.76 Found (%): C 54.09, H 4.42, N 5.76

EXAMPLE 8

Preparation of (−)-3-Acetoxymethyl-7,8-Difluoro-2,3-Dihydro-4H-[1,4]Benzoxazine-3,5-Dinitrobenzoyl Derivative (IX)

a) Ten grams of (±)-3-acetoxymethyl-7,8-difluoro-2,3-dihydro-4H-[1,4]benzoxazine (VII) as a substrate was dissolved in 1.00 liter of a mixed solvent of benzene/n-hexane (4/1 by volume). A resin in a wet state which was prepared by suspending 100 ml of DEAE-Toyopearl 650M in a 0.05M phosphoric acid buffer (pH 7.0) followed by filtration by suction and 200 mg of lipoprotein lipase (LPL Amano 3) were added to the above-prepared substrate solution. The reaction system was allowed to react at 37° C. for 6 hours under stirring. The reaction mixture was filtered by suction, and the resin was washed with 200 ml of benzene. The filtrate and the washing were combined and concentrated under reduced pressure. The concentrate weighing 9.68 g was subjected to column chromatography using 200 g of silica gel as a carrier and benzene/ethyl acetate (10/1 by volume) as an eluent to obtain 4.67 g of 3-acetoxymethyl-7,8-difluoro-2,3-dihydro-4H-[1,4]benzoxazine.

The resulting compound was dissolved in 200 ml of tetrahydrofuran, and 5.76 g of 3,5-dinitrobenzoyl chloride and 3.3 ml of pyridine were added thereto, followed by heating at 60° C. for 3 hours. The reaction mixture was concentrated under reduced pressure, and the concentrate was dissolved in 400 ml of ethyl acetate, washed successively with diluted hydrochloric acid, an aqueous solution of sodium bicarbonate and water, dried over anhydrous sodium sulfate and concentrated under reduced pressure. Addition of n-hexane to the concentrate caused precipitation of pale yellow crystals of a racemate. After sufficient precipitation, the precipitate was separated by filtration, and the filtrate was concentrated by dryness to obtain 3.93 g of a 3,5-dinitrobenzoyl derivative of the (−)-3-acetoxymethyl-7,8-difluoro-2,3-dihydro-4H-[1,4]benzoxazine (IX).

b) To about 2.0 ml of Amberlite XAD 7 was added 2.0 ml of a 0.05M phosphoric acid buffer (pH 7.0) having dissolved therein 20 mg of lipoprotein lipase (LPL Amano 3), and the system was allowed to stand at room temperature for 18 hours to thereby adsorb the enzyme onto the resin. The resin was filtered by suction and washed with 10 ml of a 0.05M phosphoric acid buffer (pH 7.0). A solution of 250 mg of (±)-3-acetoxymethyl-7,8-difluoro-2,3-dihydro-4H-[1,4]benzoxazine as a substrate in 25 ml of a mixed solvent of benzene and n-hexane (4:1 by volume) was added to the thus prepared resin in a wet state, followed by allowing to react at 37° C. for 4 hours under stirring. The reaction mixture was worked-up in the same manner as described in a) above to obtain 117 mg of optically active 3-acetoxymethyl-7,8-difluoro-2,3-dihydro-4H-[1,4]benzoxazine. In the same manner, there was obtained 65 mg of a 3,5-dinitrobenzoyl derivative of the (−)-3-acetoxymethyl-7,8-difluoro-2,3-dihydro-4H-[1,4]benzoxazine.

c) To 3.60 liters of a 0.1M phosphoric acid buffer (pH 7.0) was added 3.60 g of (±)-3-acetoxymethyl-7,8-difluoro-2,3-dihydro-4H-[1,4]benzoxazine as a substrate, and the mixture was stirred at 37° C. for 18 hours to form a solution. To the resulting solution was added 50 mg of lipoprotein lipase (LPL Amano 3), followed by allowing the system to react at 37° C. for 190 minutes while stirring. The reaction mixture was extracted three times with 2.0 liter portions of ethyl acetate. The combined extract was washed with water, dried over anhydrous sodium sulfate and concentrated under reduced pressure. The concentrate was subjected to column chromatography using 70 g of silica gel as a carrier and chloroform as an eluent to obtain 1.07 g of optically active 3-acetoxymethyl-7,8-difluoro-2,3-dihydro-4H-[1,4]benzoxazine. The resulting compound was treated in the same manner as described in a) above to obtain 0.9 g of a 3,5-dinitrobenzoyl derivative of the (−)-3-acetoxymethyl-7,8-difluoro-2,3-dihydro-4H-[1,4]benzoxazine.

d) To 3.70 liters of a 0.1M phosphoric acid buffer (pH 7.0) was added 3.70 g of (±)-3-acetoxymethyl-7,8-difluoro-2,3-dihydro-4H-[1,4]benzoxazine as a substrate, followed by stirring at 37° C. for 3.5 hours to form a solution. To the resulting solution was added 2.22 g of lipase (derived from *Candida cylindracea*), followed by allowing the system to react at 37° C. for 7.5 hours while stirring. The reaction mixture was extracted three times with 2.0 liter portions of ethyl acetate. The combined extract was washed with water, dried over anhydrous sodium sulfate and concentrated under reduced pressure. The concentrate was subjected to column chromatography using 70 g of silica gel and developed first with benzene/ethyl acetate (5/1 by volume) to elute 3-acetoxymethyl-7,8-difluoro-2,3-dihydro-4H-[1,4]benzoxazine and then with benzene/ethyl acetate (1/1 by volume) to elute 7,8-difluoro-2,3-dihydro-3-hydroxymethyl-4H-[1,4]benzoxazine.

The latter eluate weighing 1.31 g was dissolved in 60 ml of tetrahydrofuran, and 1.70 g of 3,5-dinitrobenzoyl chloride was added thereto, followed by heating at 37° C. for 20 hours. The reaction mixture was concentrated under reduced pressure, and the concentrate was dissolved in 400 ml of ethyl acetate, washed successively with a sodium bicarbonate aqueous solution and water, dried over anhydrous sodium sulfate and concentrated to dryness under reduced pressure to obtain 2.52 g of a reaction product. The reaction product was dissolved in 10 ml of pyridine, and 10 ml of acetic anhydride was added thereto, followed by heating at 37° C. for 20 hours. The reaction mixture was worked-up and recrystallized in the same manner as described in a) above to remove the racemate crystals to thereby increase optical purity. Since the product still contained slight amounts of the reaction by-products, it was further purified by Toyo-pearl HW-40-column chromatography (column: 2.5×95 cm; developing solvent: methanol/acetonitrile=1/1 by volume) and then silica gel column chromatography (column: 1.8×34 cm; developing solvent; chloroform/acetone=20/1 by volume) to finally obtain 0.44 g of a 3,5-dinitrobenzoyl derivative of (−)-3-acetoxymethyl-7,8-difluoro-2,3-dihydro-4H-[1,4]benzoxazine.

MS (m/z): 437 (M+)

$^1$H-NMR (CDCl$_3$, 200 MHz) δ(ppm): 2.14 (3H, s, —OCOCH$_3$), 4.26 (2H, d, J=7.0 Hz, —CH$_2$OCOCH$_3$), 4.45 (1H, dd, J=3.0 Hz, 12.0 Hz, C$_2$—$\underline{H}$), 4.71 (1H, d, J=12.0 Hz, C$_2$—$\underline{H}$), 4.94 (1H, m, C$_3$—$\underline{H}$), 6.60 (2H, m, aromatic ring proton), 8.73 (2H, d, J=2.0 Hz, aromatic ring proton) and 9.19 (1H, t, aromatic ring proton)

EXAMPLE 9

Preparation of (−)-7,8-Difluoro-2,3-Dihydro-3-Hydroxymethyl-4H-[1,4]Benzoxazine (VIII)

In 135 ml of tetrahydrofuran was dissolved 3.03 g of a 3,5-dinitrobenzoyl derivative of (−)-3-acetoxymethyl-7,8-difluoro-2,3-dihydro-4H-[1,4]benzoxazine, and 135 ml of ethanol and 30 ml of 1.0N potassium hydroxide were added to the solution. After the reaction mixture was stirred at room temperature for 30 minutes, 3 ml of acetic acid was added thereto for neutralization. The mixture was concentrated under reduced pressure, and the concentrate was dissolved in 400 ml of chloroform, washed successively with a sodium bicarbonate aqueous solution and water, dried over anhydrous sodium sulfate and concentrated to dryness under reduced pressure. The solid was subjected to column chromatography using 40 g of silica gel and eluted with chloroform/methanol (50/1 by volume) to obtain 1.17 g of (−)-7,8-difluoro-2,3-dihydro-3-hydroxymethyl-4H-[1,4]benzoxazine.

$[\alpha]_D^{22}$=−14.1° (c=1.80, CHCl$_3$)

$^1$H-NMR (CDCl$_3$, 200 MHz) δ(ppm): 3.5–4.4 (5H, m), 6.3–6.42 (1H, m, aromatic ring proton) and 6.54–6.74 (1H, m, aromatic ring proton)

EXAMPLE 10

Preparation of (−)-7,8-Difluoro-2,3-Dihydro-3-Methyl-4H-[1,4]Benzoxazine (X')

In 20 ml of pyridine was added 1.17 g of (−)-7,8-difluoro-2,3-dihydro-3-hydroxymethyl-4H-[1,4]benzoxazine, and 2.77 g of thionyl chloride was added thereto dropwise under ice-cooling, followed by stirring at 50° to 60° C. for 40 minutes. The reaction mixture was concentrated under reduced pressure, and the concentrate was dissolved in 300 ml of chloroform and washed with 100 ml of a sodium bicarbonate aqueous solution. The washing was extracted twice with 200 ml portions of chloroform. The combined chloroform layers were washed with water, dried over anhydrous sodium sulfate and concentrated under reduced pressure. The concentrate was subjected to column chromatography using 40 g of silica gel and eluted with chloroform to obtain 1.18 g of the reaction product as a colorless oily product. This product was dissolved in 30 ml of dimethyl sulfoxide, and 0.41 g of sodium borohydride was added thereto, followed by heating at 80° to 90° C. for 1 hour. The reaction mixture was dissolved in 500 ml of benzene, washed with water to remove the dimethyl sulfoxide, dried over anhydrous sodium sulfate and concentrated under reduced pressure. The concentrate was subjected to column chromatography using 40 g of silica gel and eluted with benzene to obtain 0.80 g of (−)-7,8-difluoro-2,3-dihydro-3-methyl-4H-[1,4]benzoxazine as a colorless oily product.

$[\alpha]_D^{25}$=−9.6° (c=2.17, CHCl$_3$)

$^1$H-NMR (CDCl$_3$, 200 MHz) δ(ppm): 1.20 (3H, d, J=6.0 Hz, —CH$_3$), 3.53 (1H, m, C$_3$—$\underline{H}$), 3.81 (1H, dd, J=8.0 Hz, 10.0 Hz, C$_2$—$\underline{H}$), 4.31 (1H, dd, J=3.0 Hz, 10.0 Hz, C$_2$—$\underline{H}$), 6.24–6.36 (1H, m, aromatic ring proton) and 6.52–6.7 (1H, m, aromatic ring proton)

Optical Purity: >99% e.e.

The product was led to the 3,5-dinitrobenzoyl derivative and quantitatively determined by HPLC using a column of Sumipacks OA-4200; 4.0×250 mm and a mixed solvent of n-hexane/1,2-dichloroethane/ethanol (90/9.1/0.9 by volume) at a velocity of 1.5 ml/min.

EXAMPLE 11

Preparation of S(−)-Ofloxacin

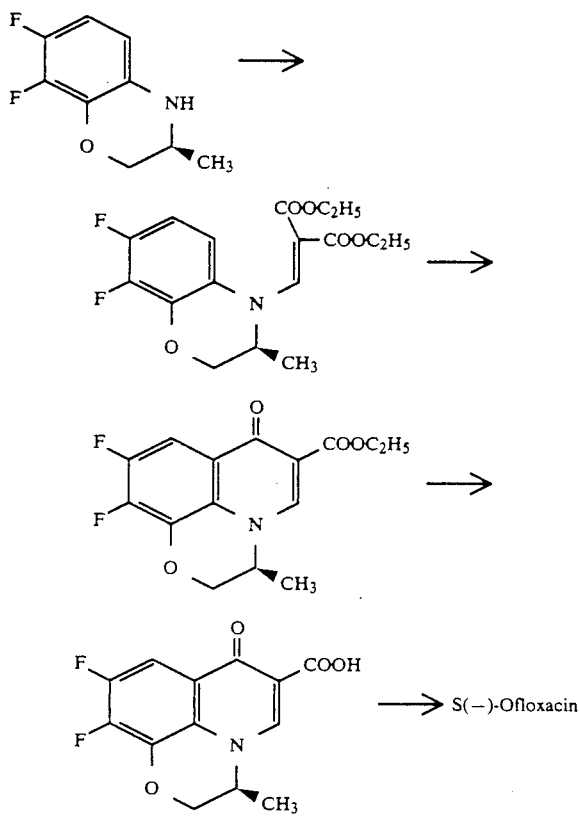

To 1.13 g of (−)-7,8-difluoro-2,3-dihydro-3-methyl-4H-[1,4]benzoxazine was added 1.58 g of diethyl ethoxymethylenemalonate, and the mixture was stirred at 130° to 140° C. for 70 minutes. The reaction mixture was subjected as such to column chromatography using 50 g of silica gel and eluted with chloroform to obtain 2.47 g of diethyl [(−)-7,8-difluoro-3-methyl-2,3-dihydro-4H-[1,4]benzoxazin-4-yl]methylenemalonate. This product was dissolved in 5 ml of acetic anhydride, and 10 ml of a mixture of acetic anhydride and concentrated sulfuric acid (2/1 by volume) with stirring under ice-cooling, followed by stirring at 50° to 60° C. for 40 minutes. To the reaction mixture were added ice and an aqueous solution of sodium bicarbonate, and the reaction product was extracted three times with 150 ml portions of chloroform. The combined extract was washed with water, dried over anhydrous sodium sulfate and concentrated under reduced pressure. When a solid began to precipitate, a small amount of diethyl ether was added thereto, and the precipitate was collected by filtration. The precipitate was washed with a small amount of diethyl ether to yield 1.32 g of (−)-ethyl 9,10-difluoro-3-methyl-7-oxo-2,3-dihydro-7H-pyrido[1,2,3-de][1,4]benzoxazine-6-carboxylate.

In 12 ml of acetic acid was dissolved 1.20 g of the resulting compound, and 25 ml of concentrated hydrochloric acid was added to the solution, followed by refluxing at 120° to 130° C. for 90 minutes. Upon allowing the reaction mixture to stand at room temperature, colorless needle-like crystals were precipitated, which were collected by filtration and washed successively with a small amount of water, ethanol and diethyl ether to obtain 0.96 g of (−)-9,10-difluoro-3-methyl-7-oxo-2,3-dihydro-7H-pyrido[1,2,3-de][1,4]benzoxazine-6-carboxylic acid.

In 30 ml of diethyl ether was suspended 324 mg of the resulting compound, and a large excess of boron trifluoride ethyl etherate was added thereto, followed by stirring at room temperature for 30 minutes to form a chelate compound. The product was collected by filtration and washed with a small amount of diethyl ether to obtain 373 mg of a powder. The powder was dissolved in 7 ml of dimethyl sulfoxide, and 136 mg of N-methylpiperazine and 228 mg of triethylamine were added thereto, followed by stirring at room temperature for 17 hours. The reaction mixture was concentrated to dryness under reduced pressure, and to the solid were added 15 ml of 95% methanol and 0.31 ml of triethylamine. The resulting mixture was refluxed for 3 hours. The reaction mixture was concentrated under reduced pressure, and the residue was filtered and washed successively with a small amount of ethanol and diethyl ether to obtain 350 mg of a white powder. Recrystallization from a mixed solvent of ethanol and thick aqueous ammonia gave 230 mg of S(−)-Ofloxacin.

Melting Point: 225°–227° C. (with decomposition).
$[\alpha]_D^{23} = -76.9°$ (c=0.39, 0.05N NaOH)
Ms (m/e): 361 (M+)
$^1$H-NMR (CDCl$_3$, 200 MHz) δ (ppm): 1.63 (3H, d, C$_3$—C$\underline{H}_3$), 2.38 (3H, s, N—C$\underline{H}_3$), 2.54–2.60 (4H, m, 2×C$\underline{H}_2$N), 3.4–3.44 (4H, m, 2×C$\underline{H}_2$N), 4.35–4.52 (3H, m, C$\underline{H}$ and C$\underline{H}_2$); 7.76 (1H, d, aromatic ring C$_8$—$\underline{H}$) and 8.64 (1H, s, C$_5$—$\underline{H}$)

EXAMPLE 12

Preparation of 3S-(+)-7,8-Difluoro-2,3-Dihydro-3-Methyl-4-[(S)-N-para-toluenesulfonylprolyl]-4H-[1,4]Benzoxazine (X″)

A solution of an acid chloride, which was prepared from 61.9 g of (S)-N-p-toluenesulfonylproline and thionyl chloride, in 350 ml of dried dichloromethane was slowly added dropwise to a solution of 32.8 g of (±)-7,8-difluoro-2,3-dihydro-3-methyl-4H-[1,4]benzoxazine and 28 ml of pyridine in 300 ml of dried dichloromethane at room temperature under stirring. The stirring was further continued for an additional 4 hours at room temperature. The reaction mixture was washed successively with 10% hydrochloric acid, a saturated aqueous solution of sodium hydrogencarbonate and a saturated aqueous solution of sodium chloride and dried over anhydrous magnesium sulfate. The dichloromethane was removed by distillation, and the oily residue was dissolved in 200 ml of ethyl acetate. To the solution was slowly added dropwise 750 ml of n-hexane while stirring whereby crystals ((−)-isomer of the compound (X″) wherein X$_1$=X$_2$=F; R$_1$=CH$_3$; R$_2$=p-toluenesulfonyl; and n=1) precipitated immediately. The precipitated crystals were separated by filtration, and the filtrate was concentrated to dryness under reduced pressure. The residue was subjected to column chromatography using 500 g of silica gel and eluted with benzene/ethyl acetate (50/1–25/1 by volume) to obtain an oily product. The oily product was dissolved in 500 ml of ethanol, and the solution was allowed to stand at room temperature for 1 day, thereby to precipitate crystals. The ethanol was distilled off, and to the thus recovered crystals were added diethyl ether and n-hexane, followed by filtration. The solid was dried under reduced pressure to obtain 33.4 g of 3S-(+)-7,8-difluoro-2,3-dihydro-3-methyl-4-[(S)-N-p-toluenesulfonyl-prolyl]-4H-[1,4]benzoxazine ((+)-isomer of the compound (X″) wherein $X_1=X_2=F$; $R_1=CH_3$; $R_2=$p-toluenesulfonyl; and n=1) having a melting point of 107°–108° C.

$[\alpha]_D = +70.7°$ (c=0.953, chloroform)

IR $\nu_{max}^{KBr}$(cm$^{-1}$): 1685, 1510, 1490

Elementary Analysis for $C_{21}H_{22}F_2N_2O_4S$: Calcd. (%): C 57.79, H 5.08, N 6.42 Found (%): C 58.05, H 5.14, N 6.47

EXAMPLE 13

Preparation of
S-(−)-7,8-Difluoro-2,3-Dihydro-3-Methyl-4H-[1,4]Benzoxazine (X)

In 1 liter of ethanol was dissolved 32.8 g of the (+)-isomer as obtained in Example 12, and 300 ml of 1N sodium hydroxide was added thereto, followed by refluxing for 3 hours. The ethanol was removed by distillation, and the oily residue was extracted with benzene. The extract was washed with a saturated aqueous solution of sodium chloride, dried over sodium sulfate and distilled to remove benzene. The residue was subjected to column chromatography using 200 g of silica gel as a carrier and benzene as an eluent to obtain 12.7 g (yield: 91.4%) of S-(−)-7,8-difluoro-2,3-dihydro-3-methyl-4H-[1,4]benzoxazine as an oily product.

$[\alpha]_D = -9.6°$ (c=2.17, chloroform)

The absolute configuration of this compound was decided to be an S-configuration by X-ray analysis on its hydrochloride.

EXAMPLE 14

Preparation of Ethyl
(S)-(−)-9,10-Difluoro-3-Methyl-7-Oxo-2,3-Dihydro-7H-Pyrido[1,2,3-de][1,4]Benzoxazine-6-Carboxylate (XII)

To 15.8 g of the (S)-(−)-benzoxazine derivative as obtained in Example 13 was added 24.0 g of diethyl ethoxymethylenemalonate, and the mixture was stirred at 130° to 140° C. for 1 hour under reduced pressure. After cooling, the reaction mixture was dissolved in 50 ml of acetic anhydride, and 80 ml of a mixture of acetic anhydride and concentrated sulfuric acid (2:1 by volume) was slowly added dropwise to the solution while stirring under ice-cooling. After continuing the stirring for additional one hour at room temperature, the reaction mixture was stirred in a hot bath of 50° to 60° C. for 30 minutes. Ice-water was added to the reaction mixture, and powdery potassium carbonate was added thereto for neutralization. The mixture was extracted with chloroform, and the extract was washed successively with a saturated aqueous solution of sodium hydrogencarbonate and a saturated aqueous solution of sodium chloride and dried over sodium sulfate. The chloroform was removed by distillation, and to the residue was added diethyl ether. The crystals thus formed were collected by filtration to give 20.0 g of the titled compound having a melting point of 257°–258° C.

$[\alpha]_D = -68.1°$ (c=0.250, acetic acid)

EXAMPLE 15

Preparation of
S-(−)-9,10-Difluoro-3-Methyl-7-Oxo-2,3-Dihydro-7H-Pyrido[1,2,3-de][1,4]Benzoxazine-6-Carboxylic Acid In 150 ml of acetic acid was dissolved 19.5 g of the ester compound obtained in Example 14, and 400 ml of concentrated hydrochloric acid was added thereto, followed by refluxing for 3 hours. After cooling, the precipitated crystals were collected by filtration, washed successively with water, ethanol and diethyl ether and dried to obtain 16.2 g of the corresponding carboxylic acid having a melting point of 300° C. or higher.

$[\alpha]_D = -65.6°$ (c=0.985, DMSO)

EXAMPLE 16

Preparation of
S-(−)-9-Fluoro-3-Methyl-10-(4-Methyl-1-Piperazinyl)-7-oxo-2,3-Dihydro-7H-Pyrido[1,2,3-de][1,4]Benzoxazine-6-Carboxylic Acid (VI) (S-(−)-Isomer of Ofloxacin In 600 ml of diethyl ether was suspended 14.3 g of the carboxylic acid obtained in Example 15, and 70 ml of boron trifluoride diethyl etherate was added thereto, followed by stirring at room temperature for 5 hours. The supernatant liquid was removed by decantation, and to the residue was added diethyl ether, followed by filtration. The solid was washed with diethyl ether and dried. The product was dissolved in 100 ml of dimethyl sulfoxide, and 14.2 ml of triethylamine and 7.3 ml of N-methylpiperazine were added to the solution. After the mixture was stirred at room temperature for 18 hours, the solvent was removed by distillation. Diethyl ether was added to the residue, followed by filtration. The collected yellow powder was suspended in 400 ml of 95% methanol, and 25 ml of triethylamine was added thereto. The mixture was heated at reflux for 25 hours. The solvent was distilled off under reduced pressure, and the residue was dissolved in 500 ml of 10% hydrochloric acid and washed three times with chloroform. The washed solution was adjusted to a pH of 11 with a 4N sodium hydroxide aqueous solution and then to a pH of 7.3 with 1N hydrochloric acid. The solution was extracted three times with 2 liter portions of chloroform, and the combined extract was dried over sodium sulfate. The chloroform was removed by distillation, and the resulting crystal was recrystallized from ethanol/diethyl ether to obtain 12.0 g of the titled compound having a melting point of 226°–230° C. (with decomposition).

$[\alpha]_D = -76.9°$ (c=0.655, 0.05N NaOH)

EXAMPLE 17

Preparation of
(S)-(−)-9-Fluoro-3-Methyl-10-(4-Ethyl-1-Piperazinyl)-7-Oxo-2,3-Dihydro-7H-Pyrido[1,2,3-de][1,4]Benzoxazine-6-Carboxylic Acid (VI)

In the same manner as described in Example 16 except that N-ethylpiperazine was used in place of N-methylpiperazine, the titled compound was obtained having a melting point of 229°–230° C. (with decomposition).

Elementary Analysis for $C_{19}H_{22}FN_3O_4$: Calcd. (%): C 60.79 H 5.91 N 11.19 Found (%): C 60.97 H 5.91, N 11.30

$[\alpha]_D = -67.0°$ (c=0.585, H$_2$O)

NMR (CDCl$_3$) δ (ppm): 1.16 (3H, t, J=7 Hz, —CH$_2$CH$_3$), 1.63 (3H, d, J=7 Hz, CH$_3$), 2.53 (2H, q, J=7 Hz, CH$_2$CH$_3$), 2.57–2.69 (4H, m, 2×CH$_2$), 3.4–3.53 (4H, m, 2×CH$_2$), 4.32–4.58 (3H, m, CH and CH$_2$), 7.77 (1H, d, J=12 Hz, C$_8$—H), 8.67 (1H, S, C$_5$—H)

While the invention has been described in detail and with reference to specific embodiments thereof, it will be apparent to one skilled in the art that various changes and modifications can be made therein without departing from the spirit and scope thereof.

What is claimed is:

1. An S(−)-pyridobenzoxazine compound represented by the formula (VI)

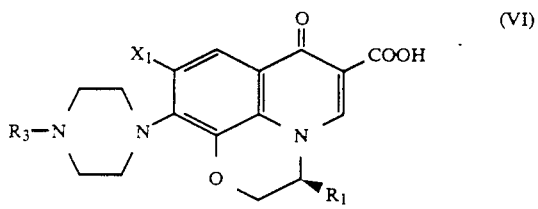

(VI)

wherein X$_1$ represents a halogen atom, R$_1$ represents an alkyl group having 1 to 4 carbon atoms, and R$_3$ represents an alkyl group having 1 to 3 carbon atoms.

2. S(−)-9-Fluoro-3-methyl-10-(4-methyl-1-piperazinyl)-7-oxo-2,3-dihydro-7H-pyrido[1,2,3-de][1,4]benzoxazine-6-carboxylic acid according to claim 1.

3. S(−)-9-Fluoro-3-methyl-10-(4-ethyl-1-piperazinyl)-7-oxo-2,3-dihydro-7H-pyrido[1,2,3-de][1,4]benzoxazine-6-carboxylic acid according to claim 1.

4. A process for treating a patient in need of an antimicrobial therapy which comprises administering to said patient an antimicrobially effective amount of an S(−)-pyridobenzoxazine compound represented by the formula (VI)

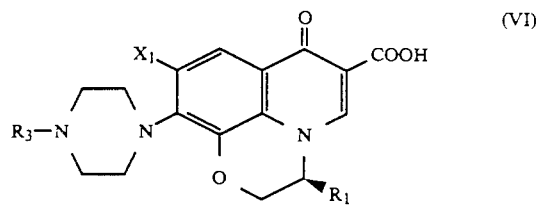

(VI)

wherein X$_1$ represents a halogen atom, R$_1$ represents an alkyl group having 1 to 4 carbon atoms, and R$_3$ represents an alkyl group having 1 to 3 carbon atoms.

5. A process for treating a patient in need of an antimicrobial therapy as in claim 4 which comprises administering to said patient an antimicrobially effective amount of S(−)-9-Fluoro-3-methyl-10-(4-methyl-1-piperazinyl)-7-oxo-2,3-dihydro-7H-pyrido[1,2,3-de][1,4]benzoxazine-6-carboxylic acid.

6. A process for treating a patient in need of an antimicrobial therapy as in claim 4 which comprises administering to said patient an antimicrobially effective amount of S(−)-9-Fluoro-3-methyl-10-(4-ethyl-1-piperazinyl)-7-oxo-2,3-dihydro-7H-pyrido[1,2,3-de][1,4]benzoxazine-6-carboxylic acid.

* * * * *

UNITED STATES PATENT AND TRADEMARK OFFICE
CERTIFICATE OF CORRECTION

PATENT NO. : 5,053,407
DATED : October 1, 1991
INVENTOR(S) : Hayakawa, et al

It is certified that error appears in the above-indentified patent and that said Letters Patent is hereby corrected as shown below:

On the title page, item [75], Inventors, please delete the names of NOBUYUKI HIGASHIHASHI and MASAYUKI OHSHIMA.

In the Abstract, line 1, delete "action" and insert --active--.

Signed and Sealed this

Twenty-seventh Day of September, 1994

Attest:

BRUCE LEHMAN

Attesting Officer

Commissioner of Patents and Trademarks